United States Patent [19]

Nickel et al.

[11] Patent Number: 5,696,074
[45] Date of Patent: Dec. 9, 1997

[54] LIQUID CRYSTALLINE, AQUEOUS SURFACTANT PREPARATIONS

[75] Inventors: Dieter Nickel, Erkrath; Rainer Hofmann, Duesseldorf; Manfred Weuthen, Solingen, all of Germany

[73] Assignee: Henkel Kommanditgesellschaft auf Aktien, Duesseldorf, Germany

[21] Appl. No.: 564,293

[22] PCT Filed: Jun. 9, 1994

[86] PCT No.: PCT/EP94/01890

§ 371 Date: Dec. 18, 1995

§ 102(e) Date: Dec. 18, 1995

[87] PCT Pub. No.: WO95/00612

PCT Pub. Date: Jan. 5, 1995

[30] Foreign Application Priority Data

Jun. 18, 1993 [DE] Germany ............... 43 20 119.9

[51] Int. Cl.$^6$ .................. C11D 3/22; C11D 3/14; C11D 11/00; C11D 17/00

[52] U.S. Cl. ............ 510/470; 510/108; 510/119; 510/130; 510/159; 510/221; 510/236; 510/337; 510/340; 510/342; 510/351; 510/356; 510/397; 510/427; 510/432; 510/497; 510/498; 510/495; 510/505; 510/507; 514/777; 514/881

[58] Field of Search ................. 510/470, 432, 510/497, 159, 221, 342, 356, 505, 337, 340, 351, 397, 498, 507; 514/777, 881

[56] References Cited

U.S. PATENT DOCUMENTS

| | | | |
|---|---|---|---|
| 3,547,828 | 12/1970 | Mansfield et al. | 252/351 |
| 4,154,706 | 5/1979 | Kenkare et al. | 252/547 |
| 4,396,520 | 8/1983 | Payne et al. | 252/89.1 |
| 4,708,813 | 11/1987 | Snyder | 510/470 |
| 5,138,046 | 8/1992 | Wuest et al. | 536/18.6 |
| 5,205,959 | 4/1993 | Schmid et al. | 252/174.17 |
| 5,306,442 | 4/1994 | Hill et al. | 252/321 |
| 5,374,716 | 12/1994 | Biermann et al. | 536/18.6 |
| 5,385,750 | 1/1995 | Aleksejczyk et al. | 427/4 |
| 5,389,282 | 2/1995 | Saijo et al. | 510/470 |
| 5,523,016 | 6/1996 | Giesen et al. | 510/470 |
| 5,527,362 | 6/1996 | Cole et al. | 510/470 |
| 5,536,437 | 7/1996 | Motyka | 510/369 |

FOREIGN PATENT DOCUMENTS

| | | |
|---|---|---|
| 070074 | 1/1983 | European Pat. Off. . |
| 92355 | 10/1983 | European Pat. Off. . |
| 092877 | 11/1983 | European Pat. Off. . |
| 105556 | 4/1984 | European Pat. Off. . |
| 132043 | 1/1985 | European Pat. Off. . |
| 132046 | 1/1985 | European Pat. Off. . |
| 301298 | 2/1989 | European Pat. Off. . |
| 357969 | 3/1990 | European Pat. Off. . |
| 362671 | 4/1990 | European Pat. Off. . |
| 0388810 | 9/1990 | European Pat. Off. . |
| 0510870 | 10/1992 | European Pat. Off. . |
| 4103696 | 4/1992 | Japan . |
| 1278421 | 6/1972 | United Kingdom . |
| Wo 8602943 | 6/1985 | WIPO . |
| WO9006300 | 6/1990 | WIPO . |
| WO9104313 | 4/1991 | WIPO . |

OTHER PUBLICATIONS

Surface Active Agents, vol. I, Interscience Publishers, 1949, p. 372.

J. Soc. Cosmetic Chemists 19, Aug. 1968, pp. 581–594.

*Primary Examiner*—Paul Lieberman
*Assistant Examiner*—Lorna M. Douyon
*Attorney, Agent, or Firm*—Wayne C. Jaeschke; John E. Drach; Henry E. Millson, Jr.

[57] ABSTRACT

Liquid crystalline aqueous surfactant compositions containing alkyl glycosides, long-chain alcohols, and, optionally, anionic surfactants; and to finished products containing them.

23 Claims, 2 Drawing Sheets

LIQUID CRYSTALLINE, AQUEOUS SURFACTANT PREPARATIONS

BACKGROUND OF THE INVENTION

1. Summary of the Invention

This invention relates to liquid crystalline, aqueous surfactant preparations of low concentration which contain alkyl glycosides and certain long-chain alcohols and optionally synthetic anionic surfactants, to a process for their production and to their use for the production of detergents or cleaning compositions.

2. Statement of Related Art

The fact that alkyl glycosides containing long-chain alkyl groups belong to the nonionic surfactants has been known for some time. The expert also knows, as described for example in A. M. Schwartz, J. W. Perry, *Surface Active Agents, Vol. I, Interscience Publishers,* 1949, page 372, that surfactant mixtures generally show synergistic effects and often have better cleaning properties than might be expected from the sum of the values of the individual components.

Detergents containing alkyl glycosides in combination with at least one typical anionic surfactant in a ratio of 1:10 to 10:1 are described in European patent application EP 070 074. Detergents containing alkyl glycosides and anionic surfactants are also known from European patent application EP 092 877. In addition, liquid detergents containing alkyl glycosides, certain other nonionic surfactants and anionic surfactants are known from European patent application EP 105 556. Alkyl-glycoside-containing liquid detergents containing typical anionic surfactants are also known from International patent application WO 86/02943. A process for the production of alkyl glycosides using catalytic quantities of an anionic surfactant in its acid form is known from European patent application EP 132 043. In European patent application EP 132 046, it is proposed to modify this production process by addition of certain bases after the actual reaction in order to neutralize the catalyst.

The alkyl-glycoside-based compounds mentioned in these documents for detergents or cleaning compositions are relatively highly concentrated aqueous solutions or pastes because the components to be mixed together to form the final formulations are intended to have as high an active substance content as possible. At the same time, they must be easy to handle, i.e. they should have a low viscosity and should be flowable and readily pumpable. By contrast, water-containing liquid products as used by the consumer, including in particular liquid detergents, dishwashing detergents and universal cleaners and also cosmetic products, for example hair shampoos or body lotions, are required to have a certain minimum viscosity although the active substance content of such products is generally relatively low. It is known from International patent application WO 91/04313 that the viscosity of detergents containing anionic and/or amphoteric surfactants is reduced by the addition of a combination of alkyl glycoside and alkali metal chloride. The alkali metal chloride content is said to be as low as possible so that the reduction in viscosity is mainly attributable to the alkyl glycoside.

Aqueous surfactant preparations containing 2 to 15% by weight of alkyl glycoside and 0.05 to 2% by weight of an anionic surfactant of the sulfate and/or sulfonate type are known from German patent application DE 41 34 071. These preparations are gel-like, isotropic viscoelastic solutions with a viscosity in the range from 250 mPa·s to 10,000 mPa·s. Accordingly, these solutions combine a desirable concentration for end products with a viscosity which is easy to handle by the consumer. However, fine-particle solids cannot readily be incorporated in the aqueous surfactant systems known from this document in such a way that they remain stable in storage, i.e. do not undergo phase separation and/or sedimentation.

For reasons of physical stability, surfactant systems which form lamellar liquid crystals are of interest for the making-up of liquid products containing undissolved solids. The occurrence of liquid crystalline phases in the water/soap system has long been known, cf. for example the review by F. B. Rosevaer in *J. Soc. Cosmetic Chemists* 19, 1968, pages 581–594. However, liquid crystals only occur in alkyl glycoside/water mixtures at very high active-substance concentrations that are virtually irrelevant so far as direct application is concerned. For example, a $C_{12/14}$ alkyl glucoside (degree of oligomerization 1.4) only forms a liquid crystalline phase ($L_\alpha$) in water at concentrations above about 65% by weight and at temperatures above 25° C. (FIG. 1).

DESCRIPTION OF THE INVENTION

Figure 1:
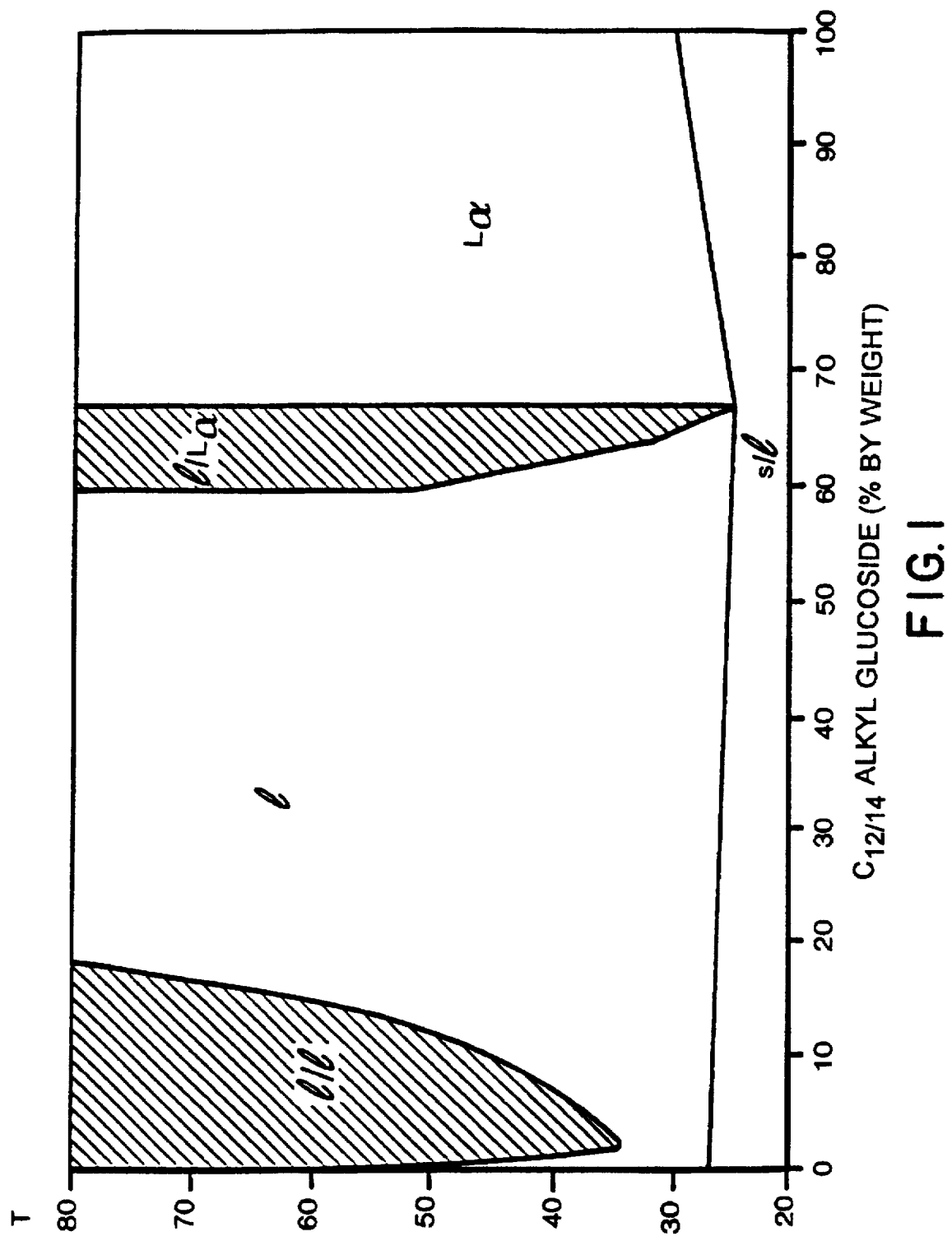
FIG. 1 shows a phase diagram of $C_{12/14}$ alkyl glucoside/water system at different temperatures.

It has now surprisingly been found that, by adding small quantities of medium- to long-chain alcohols to aqueous alkyl glycoside solutions, liquid crystals, more particularly lamellar liquid crystals, are formed even at very low alkyl glycoside concentrations. Even when anionic surfactant is added to these systems, the liquid crystalline phase structure remains intact. Instead, this addition generally leads to an applicationally favorable increase in viscosity and to the formation of a yield point.

Accordingly, the present invention relates to an aqueous surfactant preparation which contains 0.5% by weight to 30% by weight of an alkyl and/or alkenyl glycoside corresponding to formula I:

$$R^1\text{—}O(G)_n \qquad (I)$$

where $R^1$ is an alkyl or alkenyl radical containing 8 to 22 carbon atoms, more particularly 8 to 16 carbon atoms, G is a glycose unit and n is a number of 1 to 10, 0.05% by weight to 12% by weight of an alcohol corresponding to formula II:

$$R^2\text{—}OH \qquad (II)$$

where $R^2$ is an alkyl or alkenyl radical containing 6 to 20 carbon atoms and up to 3 C—C double bonds, up to 30% by weight and, more particularly, 0.01% by weight to 28% by weight of a synthetic anionic surfactant of the sulfate and/or sulfonate type, more particularly an alkyl and/or alkenyl sulfate corresponding to general formula III:

$$R^3\text{—}OSO_3M \qquad (III)$$

where $R^3$ is an alkyl or alkenyl radical containing 10 to 22 carbon atoms and up to 3 C—C double bonds and M is a cation, more particularly an alkali metal cation, and water to 100% by weight and which shows lyotropic liquid crystalline behavior at 25° C.

The present invention also relates to a process for the production of liquid crystalline, aqueous surfactant systems containing 0.5% by weight to 30% by weight of alkyl or alkenyl glycoside corresponding to formula I by mixing the glycoside with water and, optionally, up to 30% by weight, based on the surfactant system formed, of synthetic anionic surfactant of the sulfate and/or sulfonate type and alcohol corresponding to formula II in a quantity sufficient for the formation of liquid crystals at a temperature of 20° C. to 30° C., subjecting the surfactant system to intensive shearing for the purpose of homogenization and, optionally, leaving the surfactant system standing to equilibrate until the liquid crystalline phase has formed. This can take as long as 2 weeks where the individual components are used in unfavorable quantities, particularly where relatively long-chain alcohols are employed, although in general it only takes about 1.5 hours to 1 day. On a laboratory scale, the intensive shear forces required to homogenize the aqueous systems can be introduced by commercially available intensive mixers, for example Ultra-Turrax® stirrers. On a production scale, standard homogenizers or dispersers may be used. Leaving the aqueous surfactant system to equilibrate means leaving it standing at a temperature in the range from 20° C. to 30° C. The order in which the individual components are added is not important in the process according to the invention. Water in particular may be added at any stage of the production process. In a preferred embodiment, an aqueous alkyl or alkenyl glycoside solution or paste (concentration 30% by weight to 60% by weight) is initially introduced, part of the water is added, the alcohol is introduced and finally the remaining water, in which the anionic surfactant optionally to be incorporated may be present, is added.

Figure 2:
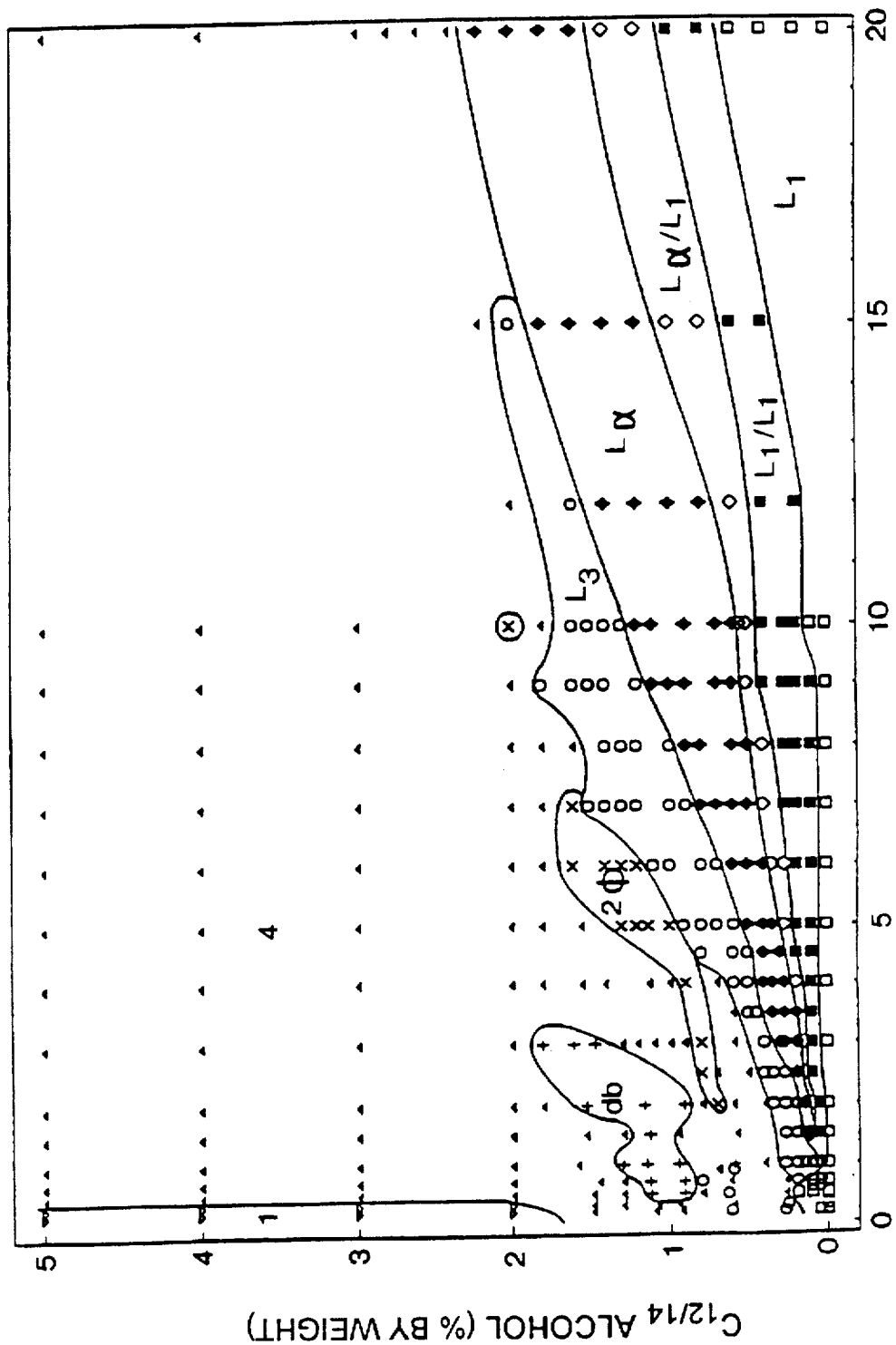
FIG. 2 shows a phase diagram of $C_{12/14}$ alkyl glucoside/ $C_{12/14}$ fatty alcohol/water system at 25° C.

It is pointed out in this connection that, in applicants' own experience, liquid crystals do not occur throughout the multicomponent system of water/alkyl or alkenyl glycoside/alcohol/optionally anionic surfactant. However, the expert is easily able to recognize the liquid crystalline systems according to the invention, for example from textures (for example band structures or spherical particle structures, as reproduced in the above-cited article by F. B. Rosevaer) under a microscope with crossed polarizers or by determining the position of the peaks and their intensity in X-ray small-angle scattering. By way of explanation, reference is made to the phase diagram in FIG. 2 of the $C_{12/14}$ alkyl glucoside/$C_{12/14}$ fatty alcohol/water system at 25° C. In this Fig., "$L_\alpha$", "db" and "$L_3$" denote liquid crystalline phases according to the invention (lamellar liquid crystalline, birefringent or streaming birefringent). The "1" phases and the "$L_1$" phases are isotropic liquid phases, two liquid isotropic phases being present in each of the regions denoted "$L_1/L_1$" and "4". A liquid crystalline phase and an isotropic liquid phase are present alongside one another in the "2φ" and "$L_\alpha/L_1$" regions.

In a preferred embodiment, the liquid crystalline preparations according to the invention contain 2% by weight to 20% by weight and, more particularly, 3% by weight to 15% by weight of alkyl or alkenyl glycoside corresponding to formula I, 0.1% by weight to 10% by weight and, more particularly, 0.5% by weight to 5% by weight of alcohol corresponding to formula II, 0.1% by weight to 25% by weight and, more particularly, 0.5% by weight to 10% by weight of synthetic anionic surfactant and water to 100% by weight. The ratio by weight of alkyl or alkenyl glycoside to alcohol is preferably 50:1 to 1:5 and, more preferably, 15:1 to 1:1. If anionic surfactant is additionally present, the quantities of alcohol are preferably somewhat higher. In this case, the ratio by weight of alkyl or alkenyl glycoside to alcohol is preferably 45:1 to 1:4 and more preferably 10:1 to 1:2.

The liquid crystalline surfactant preparations according to the invention preferably have viscosities at 25° C. in the range from 10 mPa•s to 150,000 mPa•s and, more particularly, in the range from 80 mPa•s to 10,000 mPa•s at a shear rate of 1 $s^{-1}$. It was found in this connection that particularly high viscosities occur with relatively high contents of, in particular, long-chain alcohols with $C_{12-16}$ alkyl radicals. In one preferred embodiment of the invention, therefore, the liquid crystalline surfactant preparations contain alkyl or alkenyl glycoside and $C_{12-16}$ alcohol in ratios by weight of 4:1 to 2:1 and have viscosities under the conditions mentioned in the range from 50,000 mPa•s to 150,000 mPa•s. If synthetic anionic surfactant is present, the viscosity as measured under the conditions mentioned is preferably in the range from 80 mPa•s to 12,000 mPa•s and more preferably in the range from 100 mPa•s to 10,000 mPa•s. The liquid crystalline surfactant preparations according to the invention preferably have a yield point of 0.5 Pa to 50 Pa at 25° C., particularly where they contain anionic surfactant.

The alkyl glycosides suitable for the surfactant preparations according to the invention and their production are described, for example, in European patent applications EP 92 355, EP 301 298, EP 357 969 and EP 362 671 and in U.S. Pat. No. 3,547,828. The glycoside components $((G)_n$ in formula I) of these alkyl glycosides are oligomers or polymers of naturally occurring aldose or ketose monomers, including in particular glucose, mannose, fructose, galactose, talose, gulose, altrose, allose, idose, ribose, arabinose, xylose and lyxose. The oligomers consisting of these glycoside-bonded monomers are characterized not only by the type of sugars present in them, but also by their number, the so-called degree of oligomerization. As an analytically determined quantity, the degree of oligomerization (n in formula I) may also be a broken number. In general, it assumes a value of 1 to 10 and, in the case of the alkyl glycosides preferably used, a value below 3 and, more particularly, between 1.2 and 1.4. By virtue of its ready availability, glucose is the preferred monomer unit.

The alkyl or alkenyl moiety ($R^1$ in formula I) of the alkyl or alkenyl glycosides present in the surfactant preparations according to the invention preferably also emanates from readily available derivatives of renewable raw materials, more particularly from fatty alcohols, although their branched-chain isomers, more particularly so-called oxoalcohols and/or Guerbet alcohols, may also be used for the production of useful alkyl glycosides. Accordingly, the primary alcohols containing linear octyl, decyl, dodecyl, tetradecyl, hexadecyl or octadecyl radicals and mono- or polyunsaturated alcohols with the same chain lengths, including for example oleyl alcohol, elaidyl alcohol, linoleyl alcohol, linolenyl alcohol, gadolyl alcohol and erucic alcohol, and mixtures thereof are particularly suitable. Particularly suitable alkyl glycosides contain a cocofatty alkyl radical, i.e. mixtures in which—essentially—$R^1$=dodecyl and $R^1$=tetradecyl.

It is known that the alkyl or alkenyl glycosides may contain small quantities, normally 1 to 2% by weight, based on alkyl or alkenyl glycoside, of unreacted free alcohol from their production. However, these quantities of alcohol are by no means sufficient to lead to liquid crystalline systems according to the invention.

In addition to the alcohols mentioned above, which may be starting materials for the alkyl or alkenyl glycosides, the linear or branched-chain, saturated or mono- to tri-unsaturated alcohols corresponding to formula II present in the liquid crystalline surfactant preparations according to the invention may also contain relatively short-chain alcohols, although alcohols containing less than 6 carbon atoms are not suitable for use in accordance with the invention. More particularly, the alcohols are selected from hexanol, heptanol, octanol, decanol, undecanol, 10-undecenol, dodecanol, tridecanol, tetradecanol, pentadecanol, hexadecanol, heptadecanol, octadecanol, oleyl alcohol, elaidyl alcohol, linoleyl alcohol and/or linolenyl alcohol, their linear isomers containing a primary alcohol group being preferred. The chain length of the alkyl or alkenyl moiety of the glucoside present in the liquid crystalline preparation according to the invention does not by any means have to correspond to that of the alcohol.

The anionic surfactants of the sulfate or sulfonate type optionally present in the surfactant preparations according to the invention include in particular alkyl sulfates, alkane sulfonates, alkyl benzene sulfonates, α-sulfofatty acids, carboxylic acid esters thereof, sulfonation products of alkenes or unsaturated fatty acids and mixtures thereof.

The alkyl sulfates corresponding to formula III suitable for use in accordance with the invention are known anionic surfactants which, in general, are prepared by reaction of aliphatic primary alcohols with a sulfating agent, for example sulfur trioxide or chlorosulfonic acid, and subsequent neutralization andhydrolysis of the reaction products formed, preferably with alkali metal ammonium or alkyl- or hydroxyalkyl-substituted ammonium bases. Alkyl sulfates, to which the present invention extends, are preferably derived from fatty alcohols containing 12 to 22 carbon atoms and, more particularly, 12 to 18 carbon atoms. Typical examples are lauryl alcohol, myristyl alcohol, cetyl alcohol, stearyl alcohol or behenyl alcohol. The alkyl sulfates may also be derived from the technical alcohol mixtures obtained, for example, in the hydrogenation of technical fatty acid ester mixtures of natural origin or of aldehydes from Roelen's oxo synthesis. Alkyl sulfates based on technical cocoalcohol or tallow alcohol cuts are preferred.

These alkyl sulfates may contain more or less large quantities of sulfation products of mono-, di- or tri-unsaturated alcohols with the chain lengths mentioned due to the presence of unsaturated alcohols in the starting material used for the sulfation process. Since the sulfating agent can also be added onto the double bond where unsaturated alcohols are used for the sulfation reaction, the sulfation products in question are generally mixtures of alkenyl sulfates with substances containing an internal sulfonate group or a sulfonate group and a sulfate group. In the context of the present invention, therefore, the expression "alkyl sulfate" also encompasses mixtures such as these. Where present in the alkyl sulfate, sulfation products emanating from unsaturated alcohols are preferably present in quantities of not more than 80% by weight and, more particularly, in quantities of 30% by weight to 70% by weight in the alkyl sulfate used, based on the total anionic surfactant active substance present therein.

The sulfofatty acid salts suitable for incorporation in the preparations according to the invention are neutralized derivatives of $C_{8-22}$ fatty acids containing at least one double bond. These include in particular the sulfonation products of lauroleic acid, myristoleic acid, palmitoleic acid, oleic acid, gadoleic acid and erucic acid. These sulfofatty acid salts are prepared by reaction of the unsaturated fatty acids with a sulfonating agent and subsequent neutralization and hydrolysis with the aqueous bases mentioned by known methods, for example the methods described in GB 1,278,421 and in International patent application WO 90/06300. This reaction gives mixtures of the saturated fatty acids containing a sulfo group and a hydroxy group with unsaturated fatty acids containing a sulfo group formed therefrom by formal elimination of 1 mole equivalent of water. Surface-active mixtures of hydroxyalkyl sulfonates with alkene sulfonates can be produced by an analogous reaction from alkenes preferably containing 12 to 22 carbon atoms.

α-Sulfofatty acid salts may be prepared by reaction of $C_{6-22}$ and preferably $C_{16-18}$ fatty acids preferably having an iodine value below 20 with a sulfonating agent and subsequent neutralization with aqueous bases. In this case, suitable sulfonating agents are, in particular, sulfuric acid, oleum, chlorosulfonic acid or gaseous sulfur trioxide in admixture with an inert gas. Suitable neutralization bases are, above all, aqueous solutions of alkali metal and alkaline earth metal hydroxides or ammonia. Alternatively, the esters of fatty acids of the type mentioned with $C_{1-4}$ alcohols, more particularly fatty acid methyl esters, may also be sulfonated, in which case the α-sulfofatty acid esters suitable for use in accordance with the invention are formed. They can be saponified and neutralized to form corresponding α-sulfofatty acid salts by the use of aqueous base in excess and by elimination of methanol. Typical examples of fatty acids of the type mentioned are caproic acid, caprylic acid, captic acid, lauric acid, myristic acid or behenic acid. Substances having particularly favorable detergent properties are obtained on the basis of palmitic and stearic acid which, for these reasons, are preferably used. These fatty acids may also be present in the form of the technical mixtures normally obtained in the hydrolysis of vegetable or animal fatty acid glycerol esters. If these mixtures contain large percentages of unsaturated fatty acids, they may be converted into mixtures of substantially saturated fatty acids with iodine values below 20 in known manner by hydrogenation, for example in the presence or nickel catalysts.

The alkane sulfonates suitable for use in accordance with the invention are substances obtained by sulfoxidation of hydrocarbons preferably containing 10 to 20 carbon atoms. This generally results in the formation of products with statistical distribution of the sulfonic acid substituents which, if desired, may be separated in known manner. Secondary alkane sulfonates containing 12 to 17 carbon atoms are particularly suitable for the mixtures according to the invention. In this case, too, suitable cations are, in particular, those from the group of alkali metal ions, ammonium ions or alkyl- or hydroxy-alkyl-substituted ammonium ions.

Among the synthetic anionic surfactants mentioned, alkyl sulfates, alkane sulfonates and/or sulfofatty acid esters or salts are particularly preferred.

In one preferred embodiment, a surfactant preparation according to the invention contains 3% by weight to 10% by weight of alkyl or alkenyl glycoside corresponding to formula I, 0.75% by weight to 7.5% by weight of alcohol corresponding to formula II, more particularly containing 6 to 18 carbon atoms, up to 20% by weight and, more particularly, 1% by weight to 15% by weight of synthetic anionic surfactant, more particularly of the sulfate type, and water as the balance to 100% by weight.

The liquid crystalline surfactant preparations according to the invention have excellent cleaning properties and dissolve readily in cold water. Accordingly, they are preferably used as laundry detergents, dishwashing detergents or cleaning compositions and, in particular, in hair-care and body-care products or serve as storable, easy-to-handle compounds for the manufacture of such products. In the production of corresponding end products, other constituents typically encountered in such formulations, including in particular builders, such as alkali metal tripolyphosphates, citrates, zeolites and layer silicates, corrosion inhibitors, bleaching agents, bleach activators, optical brighteners, enzymes, redeposition inhibitors, antimicrobial agents, abrasives, for example alkali metal bicarbonates or tetraborates, foam regulators and stabilizers, preservatives, pH regulators, opacifiers and pearlescers, dyes and fragrances and additional surfactants, may be added to the preparations according to the invention. The liquid crystalline surfactant preparations according to the invention are of particular advantage when fine-particle solids, for example water-insoluble builders, more particularly zeolite NaA of detergent quality, and/or abrasives, for example silica flour, marble flour or fine-particle aluminium oxide, are to be incorporated in the production of such formulations because these fine-particle solids are very effectively stabilized, i.e. are kept uniformly distributed in the liquid, by the liquid crystalline systems according to the invention. For this reason, the use of the liquid crystalline surfactant preparations according to the invention for stabilizing fine-particle water-insoluble constituents of liquid laundry detergents, cleaning products or cosmetic formulations represents a preferred application of the preparations according to the invention. It was surprising in this regard to find that the liquid crystalline surfactant preparations according to the invention are capable of stabilizing very large quantities of such water-insoluble constituents in uniform distribution. Accordingly, the liquid crystalline surfactant preparations according to the invention are preferably used in formulations, more particularly cleaners, with large percentage contents, more particularly 10% by weight to 60% by weight and, in a particularly preferred embodiment, 20% by weight to 50% by weight of water-insoluble constituents, more particularly abrasives. The quantity of surfactant system according to the invention required for stabilization is relatively small and is preferably selected in such a way that the ratio by weight of fine-particle water-insoluble constituent to the sum of alkyl and/or alkenyl glycoside corresponding to formula I and alcohol corresponding to formula II in the final formulation is in the range from 20:1 to 1:1 and, more particularly, in the range from 15:1 to 2:1.

EXAMPLES

Example 1

Aqueous mixtures M1 to M3 were prepared from the components shown in Table I below in the quantities indicated (% by weight) by mixing the individual components with an Ultra-Turrax® stirrer. All the surfactant preparations mentioned were liquid crystalline and had the indicated viscosity at 25° C. (as measured with a Carri-med® CS 100 shear-stress-controlled rotational rheometer at a shear rate D of 1 s$^{-1}$).

TABLE 1

| Viscosities of preparations according to the invention | | | |
|---|---|---|---|
| | M1 | M2 | M3 |
| $C_{12/14}$Alkyl glucoside[a] | 10 | 10 | 10 |
| $C_{12/14}$Alcohol[b] | 1 | 1.5 | 1.75 |

TABLE 1-continued

| Viscosities of preparations according to the invention | | | |
|---|---|---|---|
| | M1 | M2 | M3 |
| Water | 89 | 88.5 | 88.25 |
| Viscosity [mPa.s] | 180 | 6000 | 1000 |

[a]Degree of oligomerization 1.4
[b]Lorol® spezial, a product of Henkel KGaA

Example 2

A liquid crystalline aqueous formulation was prepared as described in Example 1 from $C_{12/16}$ alkyl glucoside (degree of oligomerization 1.4) and $C_{12/14}$ alcohol. Marble powder was added to the formulation so that a liquid cleaner M7 with the composition shown in Table 2 below was obtained. This cleaner did not lose any of its homogeneity after storage for several weeks and showed the viscosity properties indicated in Table 3, as determined with a Rheometrics® RFS II shear-stress-controlled rotational rheometer with a plate/plate measuring system (2 cm diameter, 2 mm gap).

TABLE 2

| Composition [% by weight] | |
|---|---|
| | M7 |
| $C_{12/16}$Alkyl glucoside | 5 |
| $C_{12/14}$Alcohol | 1.5 |
| Marble flour | 45 |
| Water | 48.5 |

TABLE 3

| Viscoelastic properties of M7 | |
|---|---|
| Viscosity [mPa.s] at 30 s$^{-1}$/10° C. | 1270 |
| Zero shear viscosity [mPa.s] at 10° C. | 430000 |
| Viscosity [mPa.s] at 30 s$^{-1}$/20° C. | 320 |
| Zero shear viscosity [mPa.s] at 20° C. | 330000 |
| Yield point [Pa] at 20° C. | 3.0 |
| Viscosity [mPa.s] at 30 s$^{-1}$/45° C. | 270 |
| Zero shear viscosity [mPa.s] at 45° C. | 5750000 |
| Yield point [Pa] at 45° C. | 0.3 |

List of reference numerals

FIG. 1
T: Temperature [°C.]
  1: 1 Isotropic liquid phase
  $L_\alpha$: Lamellar liquid crystalline phase
  1/1: Two-phase region (2 isotropic liquid phases)
  s/l: Two-phase region (solid and isotropic liquid)
  1/$L_\alpha$: Two-phase region (lamellar liquid crystalline phase and isotropic liquid phase)
FIG. 2
Definition of the abbreviations used in the phase diagrams
  1: Isotropic, liquid
  4: 2 Liquid phases
  db: Birefringent phase
  $L_3$: Streaming birefringent phase
  $L_\alpha$: Liquid crystalline phase
  2ϕ: Two-phase region (isotropic liquid/$L_3$)
  $L_\alpha/L_1$: Two-phase region (liquid crystalline/isotropic)

$L_1$: Isotropic liquid (micellar phase)
$L_1/L_1$: 2 Liquid phases

We claim:

1. An aqueous surfactant composition comprising:
   a) from about 0.5% by weight to about 30% by weight of at least one alkyl or alkenyl glycoside corresponding to formula I:

$$R^1\text{—}O(G)_n \quad (I)$$

where $R^1$ is an alkyl or alkenyl radical containing 8 to 22 carbon atoms, G is a glycose unit and n is a number of 1 to 10;
   b) from 0.75% to about 12% by weight of at least one alcohol corresponding to formula II:

$$R^2\text{—}OH \quad (II)$$

where $R^2$ is an alkyl or alkenyl radical containing 6 to 20 carbon atoms and up to 3 C—C double bonds;
   c) up to 30% by weight of at least one synthetic anionic surfactant which is a sulfate, sulfonate, or a sulfofatty acid ester or salt thereof;
   d) from about 20% to about 60% by weight of at least one fine particle, water insoluble component selected from the group consisting of water insoluble builders and abrasives; and
   e) water to 100% by weight;
   and wherein said composition shows lyotropic liquid crystalline behavior at 25° C. and wherein component d) is stabilized and uniformly distributed throughout said composition.

2. The composition of claim 1 wherein the ratio by weight of component a) to component b) is in the range of from about 50:1 to about 1:5.

3. The composition of claim 2 wherein said range is from 15:1 to about 1:1.

4. The composition of claim 1 wherein in component a), $R^1$ contains from 8 to 16 carbon atoms.

5. The composition of claim 1 which contains from about 0.01% to about 28% by weight of component c).

6. The composition of claim 5 wherein component c) is at least one sulfate of formula III $$R^3\text{—}OSO_3M \quad (III)$$

in which $R^3$ is an alkyl or alkenyl radical containing 10 to 22 carbon atoms and up to 3 C—C double bonds and M is a cation.

7. The composition of claim 1 wherein the composition has a viscosity, as measured at a temperature of 25° C. and at a shear rate of 1 s$^{-1}$, in the range from 10 mPa•s to 150,000 mPa•s.

8. The composition of claim 7 wherein said viscosity is in the range of from about 80 mPa•s to about 10,000 mPa•s.

9. The composition of claim 5 wherein the ratio by weight of component a) to component b) is in the range of from about 45:1 to about 1:4.

10. The composition of claim 9 wherein said range is from about 10:1 to about 1:2.

11. The composition of claim 1 wherein component a) is present in from about 2 to about 20% by weight, and component b) is present in from 0.75 to about 10% by weight.

12. The composition of claim 11 wherein from about 0.1 to about 25% by weight of component c) is present therein.

13. The composition of claim 1 wherein from about 3 to about 15% by weight of component a), from 0.75 to about 5% of component b), and from about 0.5 to about 10% by weight of component c) are present therein.

14. The composition of claim 1 wherein component b) is a $C_{12-16}$ alcohol and the ratio by weight of component a) to component b) is from about 4:1 to about 2:1.

15. The composition of claim 14 wherein the viscosity of the composition is in the range of from about 50,000 mPa•s to about 150,000 mPa•s.

16. The composition of claim 1 wherein from about 20 to about 50% by weight of component d) is present therein.

17. The composition of claim 1 wherein the ratio by weight of component d) to the sum of components a) and b) is in the range of from about 20:1 to about 1:1.

18. The composition of claim 17 wherein said range is from about 15:1 to about 2:1.

19. The composition of claim 1 wherein component a) is present in from about 3 to about 10% by weight; component b) is present in from 0.75 to 7.5% by weight; and component c) is present in up to about 20% by weight.

20. The composition of claim 19 wherein component c) is present in from about 1 to about 15% by weight.

21. In a finished composition which is a laundry detergent, a dishwashing detergent, a hair-care product, or a personal-care product, the improvement wherein a surfactant effective quantity of the surfactant composition of claim 1 is present therein.

22. A method for stabilizing fine particle, water insoluble components in a composition which is a laundry detergent, dishwashing detergent, hair-care product, or personal-care product, comprising adding to said composition a stabilizing quantity of a surfactant composition comprising
   a) from about 0.5% by weight to about 30% by weight of at least one alkyl or alkenyl glycoside corresponding to formula I:

$$R^1\text{—}O(G)_n \quad (I)$$

where $R^1$ is an alkyl or alkenyl radical containing 8 to 22 carbon atoms, G is a glycose unit and n is a number of 1 to 10:
   b) from 0.75% to about 12% by weight of at least one alcohol corresponding to formula II:

$$R^2\text{—}OH \quad (II)$$

where $R^2$ is an alkyl or alkenyl radical containing 6 to 20 carbon atoms and up to 3 C—C double bonds;
   c) up to 30% by weight of at least one synthetic anionic surfactant which is a sulfate, sulfonate, or sulfofatty acid ester or salt thereof, and
   d) water;
   wherein the fine particle, water insoluble components are selected from the group consisting of water insoluble builders and abrasives and are present in the composition in from about 20% to about 60% by weight.

23. A process for the production of a liquid crystalline aqueous surfactant composition comprising the steps of
   A) mixing together
      a) from about 0.5% by weight to about 30% by weight of at least one alkyl or alkenyl glycoside corresponding to formula I:

$$R^1-O(G)_n \quad (I)$$

where $R^1$ is an alkyl or alkenyl radical containing 8 to 22 carbon atoms, G is a glycose unit and n is a number of 1 to 10;

b) from about 0.05% to about 12% by weight of at least one alcohol corresponding to formula II:

$$R^2-OH \quad (II)$$

where $R^2$ is an alkyl or alkenyl radical containing 6 to 20 carbon atoms and up to 3 C—C double bonds;

c) up to 30% by weight of at least one synthetic anionic surfactant which is a sulfate, sulfonate, or sulfofatty acid ester or salt thereof;

d) from about 20% to about 60% by weight of at least one fine particle, water insoluble component selected from the group consisting of water insoluble builders and abrasives; and e) water;

B) applying intensive shear forces to the above mixture; and

C) letting the mixture from step B) equilibriate at a temperature of from about 20° to about 30° C. until a liquid crystalline phase has formed; wherein component d) in step A) is added either in step A) or subsequent to the preparation of the composition.

\* \* \* \* \*